(12) United States Patent
Middleton et al.

(10) Patent No.: US 9,850,460 B2
(45) Date of Patent: Dec. 26, 2017

(54) REACTOR SYSTEM

(71) Applicant: Anaero Technology Ltd, Manchester (GB)

(72) Inventors: Ray Middleton, Manchester (GB); Edgar Blanco, Manchester (GB); Robin Proctor, Manchester (GB)

(73) Assignee: ANAERO TECHNOLOGY LTD., Cambridge (GB)

( * ) Notice: Subject to any disclaimer, the term of this patent is extended or adjusted under 35 U.S.C. 154(b) by 0 days.

(21) Appl. No.: 14/909,141

(22) PCT Filed: Jul. 30, 2014

(86) PCT No.: PCT/GB2014/052339
§ 371 (c)(1),
(2) Date: Feb. 1, 2016

(87) PCT Pub. No.: WO2015/015204
PCT Pub. Date: Feb. 5, 2015

(65) Prior Publication Data
US 2016/0177249 A1    Jun. 23, 2016

(30) Foreign Application Priority Data

Jul. 31, 2013 (GB) .................................. 1313731.0

(51) Int. Cl.
*B01J 4/00* (2006.01)
*B01J 19/00* (2006.01)
(Continued)

(52) U.S. Cl.
CPC .............. *C12M 29/00* (2013.01); *B01J 4/007* (2013.01); *B01J 4/02* (2013.01); *B01J 19/1856* (2013.01);
(Continued)

(58) Field of Classification Search
CPC ..... B01J 4/00; B01J 4/001; B01J 4/007; B01J 4/02; B01J 19/00; B01J 19/0046;
(Continued)

(56) References Cited

U.S. PATENT DOCUMENTS 5,496,473 A    3/1996    Chow
5,567,122 A    10/1996   Schulte
(Continued)

FOREIGN PATENT DOCUMENTS

CA    2538499 A1    9/2007
DE    3740857 A1 *  6/1989  .............. F04B 13/02
(Continued)

OTHER PUBLICATIONS

Machine translation of DE 3740857 A1, published Jun. 15, 1989.*
(Continued)

*Primary Examiner* — Natasha Young
(74) *Attorney, Agent, or Firm* — NovoTechIP International PLLC

(57) ABSTRACT

An apparatus is described which includes at least one reactor, at least one linear piston pump, the or each piston pump including a tube, a piston and an arm coupled to the piston, the or each piston pump arranged to inject feedstock to a respective reactor, a beam or plate coupled to the arm(s) of the piston pump(s) configured to linearly drive the piston(s) and a linear actuator for driving the beam or plate. The piston pump has a volume of at least 50 milliliters and an output port having a diameter of at least 5 mm.

25 Claims, 3 Drawing Sheets

(51) Int. Cl.
| | |
|---|---|
| *B01J 19/18* | (2006.01) |
| *F04B 9/00* | (2006.01) |
| *F04B 9/02* | (2006.01) |
| *F04B 23/00* | (2006.01) |
| *F04B 23/04* | (2006.01) |
| *F04B 23/06* | (2006.01) |
| *C12M 1/00* | (2006.01) |
| *B01J 19/24* | (2006.01) |
| *B01J 4/02* | (2006.01) |
| *C12M 1/107* | (2006.01) |
| *C12M 1/02* | (2006.01) |

(52) U.S. Cl.
CPC ........... *B01J 19/24* (2013.01); *B01J 19/2445* (2013.01); *C12M 21/04* (2013.01); *C12M 23/36* (2013.01); *C12M 27/00* (2013.01); *C12M 41/18* (2013.01); *F04B 9/02* (2013.01); *F04B 23/06* (2013.01); *B01J 19/0046* (2013.01); *B01J 2219/00011* (2013.01); *B01J 2219/00058* (2013.01); *B01J 2219/00069* (2013.01); *B01J 2219/00094* (2013.01); *B01J 2219/00164* (2013.01); *B01J 2219/00166* (2013.01); *B01J 2219/00186* (2013.01); *B01J 2219/00353* (2013.01); *B01J 2219/00376* (2013.01); *B01J 2219/24* (2013.01)

(58) Field of Classification Search
CPC ........ B01J 19/18; B01J 19/1856; B01J 19/24; B01J 19/2445; B01J 2219/00–2219/00004; B01J 2219/00011; B01J 2219/00047–2219/00058; B01J 2219/00069; B01J 2219/00074; B01J 2219/00087; B01J 2219/00097; B01J 2219/00164; B01J 2219/00166; B01J 2219/00186; B01J 2219/00274; B01J 2219/00277; B01J 2219/00351; B01J 2219/00353; B01J 2219/00373; B01J 2219/00376; B01J 2219/24; C12M 21/00; C12M 21/04; C12M 23/00; C12M 23/36; C12M 27/00; C12M 41/00; C12M 41/12; C12M 41/18; F04B 9/00; F04B 9/02; F04B 23/00; F04B 23/04; F04B 23/06
See application file for complete search history.

(56) References Cited

U.S. PATENT DOCUMENTS

| | | | |
|---|---|---|---|
| 5,816,445 | A | 10/1998 | Gardos |
| 2002/0164821 | A1* | 11/2002 | Brink ................... G01F 11/021 436/180 |
| 2004/0043499 | A1 | 3/2004 | Lee-Alvarez |
| 2005/0036919 | A1 | 2/2005 | Hodson |
| 2006/0118199 | A1 | 6/2006 | Yamazaki |
| 2009/0036919 | A1 | 2/2009 | Preinitz |

FOREIGN PATENT DOCUMENTS

| | | |
|---|---|---|
| DE | 102009054532 A1 | 7/2010 |
| FR | 2950887 A1 | 4/2011 |
| WO | 2013/124456 A2 | 8/2013 |
| WO | 2013/152771 A1 | 10/2013 |

OTHER PUBLICATIONS

PCT Written Opinion from International Patent Application No. PCT/GB2014/052339.
UKIPO Search Report dated Oct. 25, 2013 for Application No. GB 1313731.0.
KDS410 Syringe Pump (available at www.kdscientific.com/products/pumps/kds410.asp) (accessed Oct. 2013).
Syringe Pump 11 Elite (available at www.warneronline.com/product_info.cfm?id=1755&name=Syringe%20Pump%2011%20Elite) (accessed Oct. 2013).
PCT/GB2014/052339 International Preliminary Report on Patentability dated Feb. 11, 2016.
International Search Report dated Nov. 4, 2014 from International Patent Application No. PCT/GB2014/052339.
GB 1313731.0 Examination Report dated Mar. 13, 2017.

* cited by examiner

REACTOR SYSTEM

CROSS-REFERENCE TO RELATED APPLICATIONS

This application is a National Stage of International patent application PCT/GB2014/052339, now WO 2015/015204, filed on Jul. 30, 2014, which claims priority to foreign patent application No. GB 1313731.0, filed on Jul. 31, 2013, the disclosures of which are each incorporated by reference in their entireties.

FIELD OF THE INVENTION

The present invention relates to a reactor system, in particular to a chemical or biochemical reactor system, and more particularly to a bench- or laboratory-scale chemical or biochemical reactor system.

BACKGROUND

Syringe pumps can be used in medical and small-scale laboratory research applications, such as biochemical and microfluidic applications, to dispense a fluid, such as a drug or reagent, at a controlled rate.

Examples of syringe pumps include syringe pumps marketed by KD Scientific Inc., Holliston, Mass., United States and by Warner Instruments, Hamden, Conn., United States. Examples of syringe pumps are also described in US 2005/0036919 A1 and US 2004/0043499 A1, FR 2 950 887 A1, DE 10 2009 054 532 A1 and CA 2 5 38 499 A1. An arrangement can be employed which uses multiple syringes and an example of such an arrangement is described in US 2009/0035825 A1. In many of these examples, the syringe pumps are used in polymerase chain reaction (PCR) reactors.

Syringe pumps, particularly those used in medical and PCR applications, are typically used to dispense fluids containing small particles, i.e. usually having particle sizes no more than 1 mm, and low dry solids content, i.e. normally no more a few percent. These syringe pumps also employ small syringes, i.e. having volumes up to around 100 ml).

SUMMARY

According to a first aspect of the present invention there is provided apparatus comprising at least one reactor. The apparatus comprises at least one linear piston pump (which may be referred to as a "syringe"), the or each piston pump including a tube, a piston and an arm coupled to the piston, the or each piston pump arranged to inject feedstock to a respective reactor. The apparatus comprises a beam (or "bar") or plate coupled to the arm(s) of the piston pump(s) configured to linearly drive the piston(s). The apparatus comprises a linear actuator for driving the beam or plate.

The, or each, piston pump has a volume of at least 50 milliliters and a discharge port having a minimum diameter of 5 mm. The volume may be at least 100 milliliters, at least 200 milliliters, at least 500 milliliters or at least 1 liter and/or no more than 2 liters, no more than 5 liters, no more than 10 liters or no more than 20 liters. The, or each, discharge port may have a minimum diameter of 10 mm, 20 mm, 50 mm, 1 cm, 2 cm or 5 cm and/or a maximum diameter of ii cm or 16 cm.

Thus, the system can be used to supply the feedstock to the reactor(s) continuously over considerable periods (e.g. 10, 20, 30 days or more, even up to 150 days), for example, without needing to open the reactor(s). This allows the apparatus to mimic industrial-scale reactors, for example, which are continuous flow and/or capable of holding thousands of tonnes of wastewater.

The apparatus may comprise at least two reactors and at least two piston pumps. The beam or plate may be configured to linearly drive the pistons at the same time.

According to a second aspect of the present invention there is provided apparatus comprising at least one chemical or biochemical reactor. The apparatus comprises at least one linear piston pump, the or each piston pump including a tube having a closed end, an orifice in the closed end of the tube, a piston and an arm coupled to the piston which is arranged to move along an axis of travel, the or each piston pump arranged to inject feedstock to a respective reactor. The apparatus comprises a beam or plate coupled to the arm(s) of the piston pump(s) configured to linearly drive the piston(s). The apparatus comprises a linear actuator for driving the beam or plate.

The apparatus may comprise an array of at least two reactors and an array of at least two piston pumps. The piston pumps may be arranged such that the axes of travel are aligned in parallel and the beam or plate may be configured to linearly drive the pistons at the same time.

The linear actuator may comprise a rotary motor and a device, such as a screw, for converting rotary motion into linear motion.

The apparatus may comprise at least 6 reactors. The apparatus may comprise between 6 and 9 reactors. The apparatus may comprise at least 12 reactors, at least 24 reactors or at least 36 reactors.

The, or each, reactor may have a volume of at least 100 milliliters, at least 1 liter, at least 2 liters or at least 5 liters and/or no more than 5 liters, no more than 10 liters, no more than 20 liters, no more than 50 liters or no more than 100 liters. The, or each, reactor may have a volume of about 5 liters.

Each piston pump has a volume, $V_P$, which may be at least one tenth, at least one-twentieth or at least one-fiftieth of the reactor volume. The piston pump volume may be no more than one-fiftieth of the reactor volume or one-hundredth of the reactor volume.

The, or each, reactor and the, or each, piston pump may have given volumes and the linear actuator may be operable at a given rate such that the retention time of at least 10 days or at least 20 days and/or no more than 30 days, no more between 50 days no more than 100 days or no more than 200 days. The, or each, piston pump may be cooled or heated. The piston pump may include a mixer for agitating feedstock before feeding.

The, or each, piston pump may be capable of injecting feedstock comprising a total solids content of at least 0.05 mass percent, of at least 0.1 mass percent, of at least 0.2 mass percent, of at least 0.5 mass percent, of at least 1 mass percent, of at least 2 mass percent, of at least 5 mass percent, of at least 10 mass percent or of at least 20 mass percent and/or no more than 40 mass percent.

The apparatus may further comprise at least one spent collector, the, or each, spent collector in fluid communication with a respective reactor.

The, or each, reactor may include a respective port for collecting product gases. The apparatus may further comprise at least one gas-over-water tumbler collector for measuring rate of gas production, each collector in fluid communication with a respective reactor.

The, or each, reactor may be provided with a respective heater jacket.

The, or each, reactor may be provided with a respective thermocouple.

The, or each, reactor may be provided with an internal rotating agitator (such as a paddle, blade, etc) for mixing feedstock in the reactor. The apparatus may further comprise a drive mechanism for driving the paddles.

The apparatus may be a bench- or laboratory-scale reactor system.

The feedstock may be wastewater, such as sewage, food waste and/or combination of liquids and solids up to a solids content of 40 mass percent.

BRIEF DESCRIPTION OF THE DRAWINGS

Certain embodiments of the present invention will now be described, by way of example, with reference to the accompanying drawings in which.

DETAILED DESCRIPTION OF CERTAIN EMBODIMENTS

Small-scale reactor systems can be used to model large-scale production plants. For example, a small-scale reactor system which consists of several (e.g. up to 9) reactors and which is controlled by a processor can be used to mimic the behaviour and reactions of a larger installation. Such a system, however, is usually fed with a feedstock on a daily basis in a single shot. However, this approach can provide misleading results since a large-scale plant is typically fed continuously or effectively continuously (for example, by using several small batches each day) and current bench-scale digesters up to now have relied on manual feeding once a day.

Figure 1:
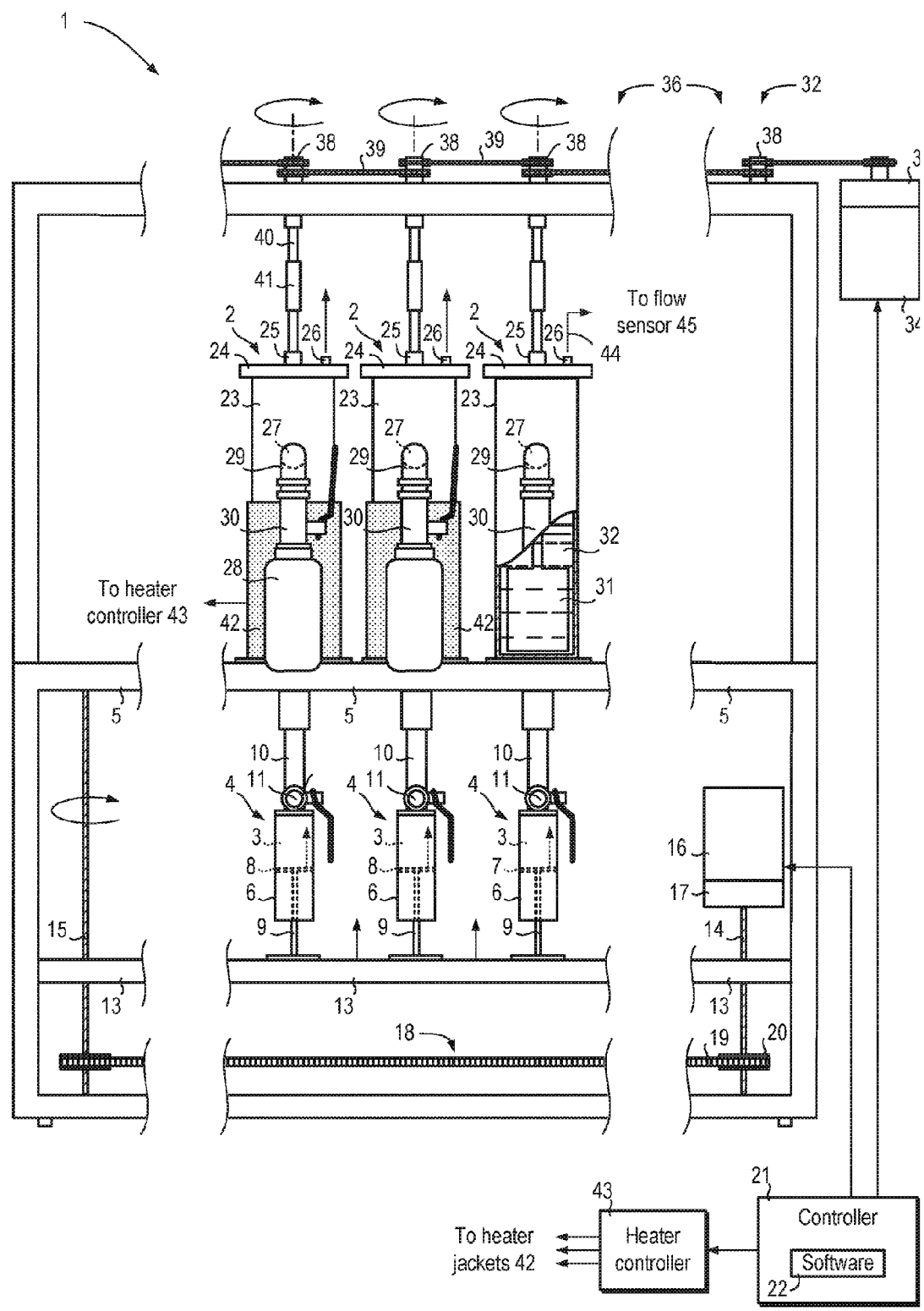
FIG. 1 is a front view of a reactor system.

Referring to FIG. 1, a bench- or laboratory-scale reactor system 1 is shown which includes one or more reactors 2. The system 1 can be used to introduce feedstock 3 continuously and controllably into the one or more reactors 2 and enable a large-scale, continuous processing system to be accurately modelled.

In this example, the reactor system 1 is used to model a large-scale, continuous anaerobic digester which can process biodegradable waste, such as waste food and/or sewage. However, the reactor system 1 can be used to model large-scale reactor-based processing systems.

Figure 2:
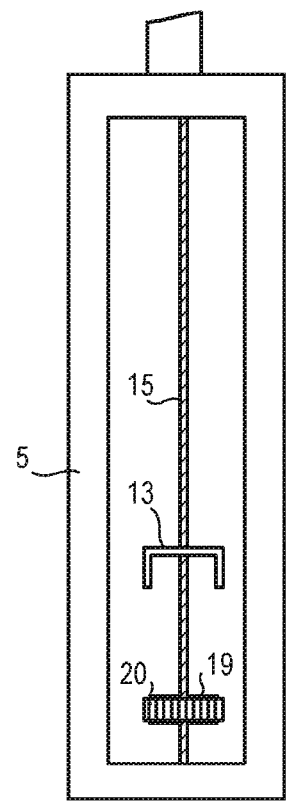
FIG. 2 is a side view of a part of the reactor system shown in FIG. 1.
Figure 3:
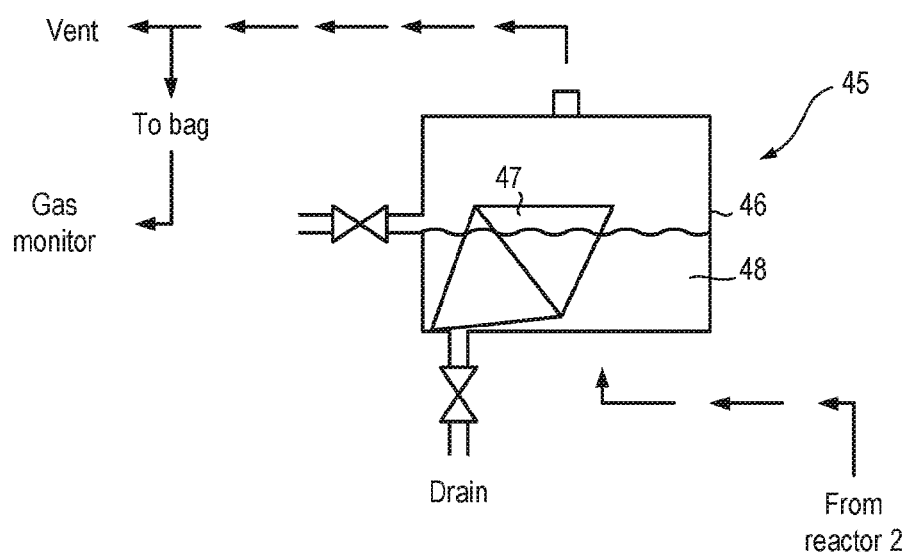
FIG. 3 is a schematic diagram of a gas tumbler system.

Referring to FIGS. 1, 2 and 3, the reactor system 1 includes one or more reactors 2 and a corresponding number of linear piston pumps 4 (or "syringes") for introducing respective charges of feedstock 3 into the reactors 2. The reactors 2 are generally cylindrical and are formed from stainless steel. Each reactor 2 has a volume, $V_R$, which is preferably at least 5 liters. The reactors 2 are supported in a frame 5 and are arranged, in this example, in a single, horizontal row (or "bank").

Each piston pump 4 consists of a tube (or "barrel") 6 having a discharge port 7 (FIG. 4), a piston 8 and an arm 9 coupled to the piston 8. The piston 8 and arm 9 may be referred to as a "plunger". Fluid communication between a reactor 2 and a corresponding piston pump 4 is provided by a pipe 10. A valve 11, in this case a 3-way 'T'-shaped valve, is provided between each piston pump 4 and the pipe 10 to allow interchange of a spent piston pump 4 for another charged with feedstock. The piston pumps 4 may be formed from any suitable material. In this example, the piston pumps 4 are formed from plastic.

The piston pumps 4 are arranged in a single horizontal row under the reactors 2. The piston pumps 4 introduce feedstock 3 via respective charge ports 12 (see FIG. 4) in the bases of the reactors 2. Each piston pump 4 has a volume, $V_P$, which is preferably at least one-fiftieth of the reactor volume, $V_R$, i.e. $V_P \geq 0.02 \, V_R$. In this case, the piston pumps 4 have a volume, $V_P$, or 600 ml. Each piston pumps 4 can, however, have a volume of up to 5 or 6 liters or more.

The barrels 6 of the piston pumps 4 are held in fixed positions, in this case, by virtue of being attached to corresponding reactors 2 via the pipes 10, which are rigid. However, the piston pumps 4 can be held in place using other arrangements, such as clamps and/or frames.

The reactor system 1 includes a moveable beam 13 coupled to the arms 9 of the piston pumps 4. Thus, the beam 13 can linearly drive the piston pumps 4.

The beam 13 is driven upwards by first and second drive shafts 14, 15. The first drive shaft 14 is coupled to an electric motor 16 via a constant-speed, high-reduction motor and gearbox 17. The second drive shaft 15 is coupled to the first drive shaft 14 by a chain drive 18 which includes one or more chains 19 and two or more sprockets 20. The chain drive 19 and sprocket 20 can be replaced by a shaft and gear array, or by a motor/reduction gearbox fitted directly to the drive shaft 14 and/or 15.

Continuous upward movement of the beam 13 causes the piston pumps 4 to introduce feedstock 3 into the reactors 2 in parallel, at a pre-determined rate. The motor/gearbox 16 can rotate at 2 revolutions per hour which may be converted into linear motion having a rate, for example, of 1 mm per hour or more or 10 mm per hour or more. Thus, feed rates of orders of magnitude of 0.1, 1, 10 or 100 milliliters a day can be achieved. These feed regimes can be used to provide a reactor time of residence of 10 days or more or 100 days or more. Using interchangeable piston pumps 4, feeds regimes can last 3 days or more or 10 days or more.

The system 1 is controlled by a programmable process controller 21 which may be provided with a HMI touch screen (not shown). The controller 21 runs computer software 22 and can be used to provide flexible multi-feed regimes that can be constant or progressive. The system 1 can also be controlled by a programmable on/off timing device to switch motor 16 at required intervals.

Each reactor 2 is operated as an independent system. Each reactor 2 is separate from the other reactors 2 and can be sealed. Each reactor 2 includes a reactor housing 23 and a removable lid 24 which includes a stirrer port 25 and a gas outlet port 26. Other ports may be provided to allow dosing and/or sampling tests.

Each reactor 2 includes a side port 27 which allows spent fluid to flow out from the reactor 2 and be collected in a bottle 28. Fluid communication between a reactor 2 and a corresponding collector bottle 28 is provided by an elbow connector 29. A valve 30, in this case a 3-way 'T'-shaped valve, is provided between each collector bottle 28 and the connector 29 to allow interchange of bottles 28.

Each reactor 2 is provided with a rotatable paddle 31 coupled to a constant drive system 32. The paddle 31 is used to help ensure that the content 33 of a reactor 2 is, as far as is practicable, homogenous. It can also assist the release gases and so mimic large plant mixing techniques.

The drive system 32 includes a motor 34 and gearbox 35 coupled to a chain drive 36. The chain drive 36 may include multiple stages to allow more than one paddle 31 to be driven. The chain drive system 36 includes one or more chains 37 and two or more sprockets 38. The chains 37 and sprockets 38 can be replaced by shafts and transmission gearboxes in some applications. The paddles 31 are coupled to the chain drive 36 via spindles 40 and connectors 41. The connectors 41 can be de-coupled from the spindle 40 and paddle shaft so as to allow servicing or replacements of reactors 42. The connectors 41 may be formed from plastic tubing.

It is possible to control the rate of mixing and also start and stop the mixing motor 34. This ensures that it is possible to accommodate a range of desired mixing regimes required for the testing.

Each reactor 2 has a heater jacket 42 and a thermocouple (not shown) so that the temperature of each reactor 2 can be independently controlled using heater controller 43. For example, the temperature of the reactors 2 may be set to a temperature, T, which may lie in a range up to a temperature of 90° C. or 145° C. As the reactors 2 are made of stainless steel and high-temperature plastic, the reactors 2 can be used as pasteurisers, or hydrolyser (biological or thermal), if required. The reactors 2 can operate at atmospheric pressure.

Gas 44 from each reactor 2 flows via piping (not shown) to respective mass flow sensors 45. Each sensor 45 takes the form of a gas tumbler having a housing 46 which contains a pivoted trapezoidal block 47 and which is partially filled with water 48. As gas 44 enters the tumbler 45, it is trapped under the block 47 which is initially in a rest position. A volume of gas begins to collect and starts to lift one side of the block 47. This continues until a sufficiently large volume of gas has been collected which tilts the block 47 enough to allow the volume of gas 44 to escape. The block returns to its rest position (i.e. it tumbles) and the process is repeated. The volume of gas needed to tip the block 47 is known and by counting each time the block tumbles (for example using a magnet connected to the block and a reed switch), the total volume of gas can be calculated. To maintain accurate measurement, the ambient temperature and atmospheric pressure are recorded at the point of each tumble. Thus, mass (stp) values can be delivered by the system.

To further enhance tumbler accuracy, water levels are pre-set to afford efficient tumbling and by operator sample calibration after water changes or at pre-determined intervals system accuracy can be maintained.

Ensuring that all important accumulation of system error is held to a minimum and that recorded data is viable.

The post-tumbled gas 44 can either be vented to atmosphere or collected in bags for gas quality measurement.

The reactor system 1 employs piston pumps 4 and a piston pump driving arrangement which can be used to model a continuous large scale plants. Conventional pump syringes cannot be used for one or more reasons. First, the feedstock 3 can have a high dry solid content, i.e. 30% or more, and/or large particle size, i.e. 10 mm or more, which would block a conventional pump syringe. Secondly, conventional pump syringes tend to have a capacity of up to around boo milliliters which limits the size of the reactor 2.

Figure 4:
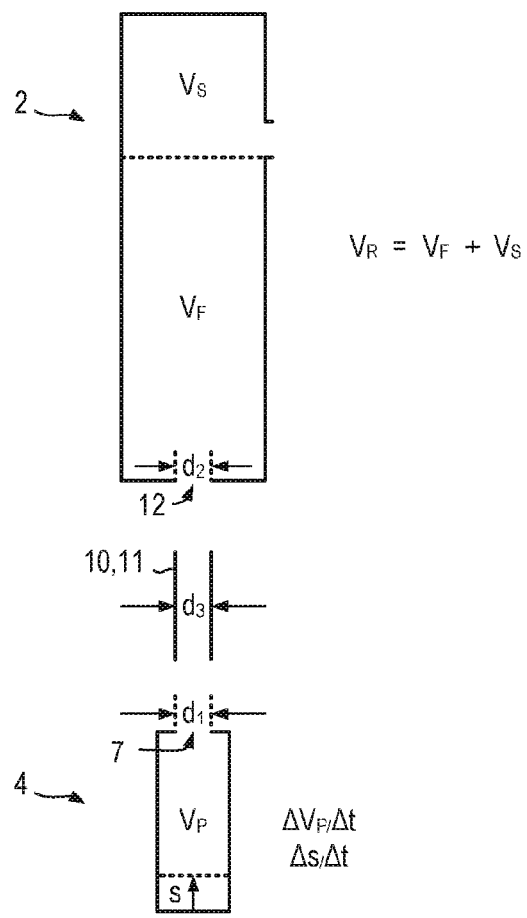
FIG. 4 illustrates a reactor and a pump piston.

FIG. 4 is a schematic diagram of the reactor system 1 illustrating volumes of the reactor 2 and piston pump 4 and diameters of the piston pump discharge port 7 and the reactor charge port 12 and interconnecting pipework 10, 11.

The piston pump 4 has a discharge port 7 having a minimum diameter, $d_1$, of at least 5 mm and up to 10.16 cm (4"). The reactor has a charge port 12 having a minimum diameter, d2, of at least 5 mm and up to 10.16 cm (4"). The pipework 10, 11 connecting the ports 7, 11 have a minimum diameter, d3, of at least 5 mm.

It will be appreciated that many modifications may be made to the embodiments hereinbefore described. For example, the syringes may be inverted and the beam may push the plungers down. For example, the syringes may be arranged horizontally and the beam may push the plungers sideways. The syringes may be arranged in a two-dimensional array and a set of beams or plate (e.g. a rectangular plate) can urge the syringe arms.

The invention claimed is:

1. An apparatus comprising:
   at least one reactor;
   at least one linear piston pump, the or each piston pump including a tube, a piston and an arm coupled to the piston, the or each piston pump arranged to inject feedstock to a respective reactor, the piston pump having a volume of at least 50 milliliters and an output port having a diameter of at least 5 mm;
   a beam or plate coupled to the arm(s) of the piston pump(s) configured to linearly drive the piston(s); and
   a linear actuator for driving the beam or plate.

2. The apparatus according to claim 1, comprising at least two reactors and at least two piston pumps, wherein the beam or plate is configured to linearly drive the pistons at the same time.

3. The apparatus according to claim 1, wherein the volume is no more than 10 liters or no more than 20 liters.

4. The apparatus according to claim 1, wherein the diameter is no more than 11 cm or no more than 16 cm.

5. The apparatus according to claim 1, wherein the linear actuator comprises:
   a rotary motor; and
   a device for converting rotary motion into linear motion.

6. The apparatus according to claim 5, wherein the device comprises a screw.

7. The apparatus according to claim 1, which comprises at least 6 reactors.

8. The apparatus according to claim 1, wherein the or each reactor has a volume of at least 100 milliliters, at least 1 liter, at least 2 liters or at least 5 liters and/or no more than 5 liters, no more than 10 liters, no more than 20 liters, no more than 50 liters or no more than 100 liters or more.

9. The apparatus according to claim 1, wherein the or each piston pump has a volume of at least 50 milliliters, at least 100 milliliters, at least 200 milliliters, at least 500 milliliters, at least 200 milliliters, at least 500 milliliters, at least 1 liter, at least 2 liters, at least 5 liters or at least 10 liters.

10. The apparatus according to claim 1, wherein the or each reactor and the or each piston pump have given volumes and the linear actuator is operable at a given rate such that the retention time of at least 10 days or at least 20 days and/or no more than 30 days, no more than 50 days, no more than 100 days, or no more between 150 days.

11. The apparatus according to claim 1, wherein the or each piston pump is capable of injecting feedstock comprising a total solids content of at least 0.05 mass percent, of at least 0.1 mass percent, of at least 0.2 mass percent, of at least 0.5 mass percent, of at least 1 mass percent, of at least 2 mass percent, of at least 5 mass percent, of at least 10 mass percent or of at least 20 mass percent and/or no more than 40 mass percent.

12. The apparatus according to claim 1, wherein the discharge port may have a minimum diameter of 10 mm, 20 mm, 50 mm or 100 mm.

13. The apparatus according to claim 1, further comprising:
   at least one spent collector, the or each spent collector in fluid communication with a respective reactor.

14. The apparatus according to claim 1, wherein the or each reactor includes a respective port for collecting product gases.

15. The apparatus according to claim 14, further comprising at least one gas-over-water tumbler collector for measuring rate of gas production, each collector in fluid communication with a respective reactor.

16. The apparatus according to claim 1, wherein the or each reactor is provided with a respective heater jacket.

17. The apparatus according to claim 1, wherein the or each reactor is provided with a respective thermocouple.

18. The apparatus according to claim 17, further comprising a drive mechanism for driving the mixer(s).

19. The apparatus according to claim 1, wherein the or each reactor is provided with a mixer, such as a paddle, for mixing feedstock in the reactor.

20. The apparatus according to claim 1, which is a bench- or laboratory-scale reactor system.

21. The apparatus according to claim 1, wherein the feedstock is wastewater, such as sewage, food waste and/or combination of liquids and solids up to a solids content of 40 mass percent.

22. The apparatus according to claim 1, wherein the or each reactor is a chemical or biochemical reactor.

23. The apparatus according to claim 1, wherein each tube has a closed end and an orifice in the closed end of the tube and wherein the piston and arm are coupled the piston, the or each piston pump being arranged to move along an axis of travel.

24. An apparatus comprising:
at least one chemical or biochemical reactor;
at least one linear piston pump, the or each piston pump including a tube having a closed end, an orifice in the closed end of the tube, a piston and an arm coupled to the piston which is arranged to move along an axis of travel, the or each piston pump arranged to inject feedstock to a respective reactor, the piston pump having a volume of at least 50 milliliters and an output port having a diameter of at least 5 mm;
a beam or plate coupled to the arm(s) of the piston pump(s) configured to linearly drive the piston(s); and
a linear actuator for driving the beam or plate.

25. The apparatus according to claim 24, comprising at least two reactors arranged in a row and at least two piston pumps arranged in a row, wherein the at least two piston pumps are arranged such that the axes of travel are aligned in parallel and wherein the beam or plate is configured to linearly drive the pistons at the same time.

* * * * *